US008486453B2

(12) United States Patent
Chen et al.

(10) Patent No.: US 8,486,453 B2
(45) Date of Patent: Jul. 16, 2013

(54) CONTROLLED RELEASE COMPOSITIONS WITH REDUCED FOOD EFFECT

(75) Inventors: Shou-Chiung Chen, Chiayi (TW); Shao-Ming Lee, Xizhi (TW); Chaur-Ming Jan, Coral Springs, FL (US)

(73) Assignee: TWI Pharmaceuticals, Inc. (TW)

( * ) Notice: Subject to any disclaimer, the term of this patent is extended or adjusted under 35 U.S.C. 154(b) by 0 days.

(21) Appl. No.: 13/164,995

(22) Filed: Jun. 21, 2011

(65) Prior Publication Data

US 2011/0311594 A1    Dec. 22, 2011

Related U.S. Application Data

(60) Provisional application No. 61/357,251, filed on Jun. 22, 2010.

(51) Int. Cl.
*A61K 9/24* (2006.01)

(52) U.S. Cl.
CPC .................................... *A61K 9/209* (2013.01)
USPC .......................................................... 424/472

(58) Field of Classification Search
None
See application file for complete search history.

(56) References Cited

U.S. PATENT DOCUMENTS

| 6,372,255 | B1 | 4/2002 | Saslawski et al. |
| 6,495,162 | B2 * | 12/2002 | Cheng et al. .................. 424/464 |
| 7,214,387 | B2 | 5/2007 | Sanghvi et al. |
| 2003/0187074 | A1 * | 10/2003 | Hussain et al. ............... 514/635 |
| 2004/0106660 | A1 | 6/2004 | Kositprapa et al. |
| 2005/0158374 | A1 * | 7/2005 | Wong et al. ................... 424/450 |
| 2006/0134206 | A1 * | 6/2006 | Iyer et al. ...................... 424/468 |
| 2012/0041069 | A1 * | 2/2012 | Sesha ............................ 514/635 |

* cited by examiner

*Primary Examiner* — Bethany Barham
(74) *Attorney, Agent, or Firm* — Wood, Phillips, Katz, Clark & Mortimer

(57) ABSTRACT

The present invention provides a controlled release pharmaceutical composition which exhibits reduced food effect.

27 Claims, No Drawings

CONTROLLED RELEASE COMPOSITIONS WITH REDUCED FOOD EFFECT

BACKGROUND OF THE INVENTION

Oral administration of drugs is frequently affected by food-drug interactions, a phenomenon often described by the term "food effect". As generally interpreted, food effect is a very broad term which refers to all aspects of interactions of food on drug dissolution, absorption, distribution, metabolism and elimination. The implications of food effect include changes in bioavailability, rate of on-set, duration of therapeutic effect and incidence and seriousness of side effects.

The food effect is an important issue during the development of a drug. In some cases where food-drug interactions lead to an increase of drug absorption, the drug formulation is recommended to be taken with food in order to be sufficiently absorbed and exert its expected clinical effect. However, such drug formulations are not preferred because drug absorption can vary with food types and quantity. For example, if a patient forgets to take the drug formulation with food, the drug may be poorly absorbed and therefore not clinically efficient. This problem may be avoided by a formulation without food effect.

Thus, there is a need for new sustained release compositions with reduced or no significant food effect.

Metformin is an oral antihyperglycemic drug of the biguanide class used in the management of non-insulin-dependent diabetes mellitus (NIDDM). It has been widely prescribed for lowering blood glucose in patients with NIDDM.

The benefits of a sustained release dosage form of metformin have been well known: it allows one to simplify the patient's administration scheme by reducing the amount of recommended daily intakes, improves patient compliance, and attenuates adverse events, e.g., related to high plasma peaks. Immediate release compositions of metformin exhibit negative food effect when orally administered to a subject.

The commercially available sustained-release dosage forms of metformin, such as Glucophage® XR, Glumetza® and Fortamet®, have significant positive food effect. Thus, they are all recommended to be taken with food to increase drug bioavailabiltiy and maximum therapeutic benefits.

Thus, there is a need for new sustained release compositions of metformin with reduced or no significant food effect.

SUMMARY OF THE INVENTION

In one embodiment, the present invention provides a controlled release pharmaceutical composition which exhibits reduced food effect as compared to conventional controlled release compositions, wherein said composition comprises an active agent (which may be referred to as a "drug") which has a limited window of absorption and displays a negative food effect when an immediate release dosage form of the drug is orally administered to a subject.

In one embodiment, the invention provides a controlled release pharmaceutical composition which exhibits reduced food effect as compared to conventional controlled release formulations, said composition comprising:
  (a) a sustained release layer comprising:
    (i) an active agent, wherein said active agent has a limited window of absorption and displays a negative food effect when an immediate release formulation of said active agent is orally administered to a subject;
    (ii) optionally, at least one release modifier; and
    (iii) at least one sustained release agent; and
  (b) an immediate release layer comprising said active agent and at least one pharmaceutically acceptable excipient.

In one embodiment, the active agent is metformin.

In one embodiment, the invented controlled release pharmaceutical composition further comprises a second therapeutic agent.

In another embodiment, the invention provides a controlled release pharmaceutical composition of metformin, wherein the bioavailability of metformin is not increased more than 50% when said controlled release composition is orally administered to a subject in the fed state.

In yet another embodiment, the invention provides a method of reducing the food effect of a controlled release composition, said method comprising a step of formulating an active agent into a unit dosage form, wherein the unit dosage form comprises at least one sustained layer and one immediate release layer.

In yet another embodiment, the invention provides a method of reducing the time necessary to reach steady state for metformin, said method comprising administering a controlled release composition of metformin to a subject in need thereof, wherein the controlled release composition has higher bioavailability than a comparable dose of Fortamet® (metformin hydrochloride) tablets.

In yet another embodiment, the invention provides a method of improving the bioavailability of a controlled release dosage form of metformin in a fasted mode, said method comprising formulating metformin into a dosage from comprising a sustained release layer and an immediate release layer, wherein metformin is present in both the sustained release layer and the immediate release layer.

In yet another embodiment, the invention provides a method of manufacturing a matrix controlled release tablet, said method comprising: (a) mixing a portion of an acid salt form of an active ingredient with an alkaline agent to form a mixture; (b) granulating said mixture with a controlled release agent; and (c) compressing the granules from step (b) into tablets.

DEFINITIONS

The term "food effect", as used herein, refers to a relative difference in AUC (Area under the curve), $C_{max}$ (Maximum plasma concentration), and/or $T_{max}$ (Time to maximum concentration) of an active substance, when said substance or a formulation thereof, such as a tablet or a capsule, is administered orally to a mammal, preferably a human, concomitantly with food or in a fed state as compared to the same values when the same formulation is administered in a fasted state. The food effect F is calculated as $$F=(Y_{fed}-Y_{fasted})/Y_{fasted}$$

wherein $Y_{fed}$ and $Y_{fasted}$ are the found values of AUC, $C_{max}$ or $T_{max}$ in the fed and fasted state, respectively.

The term "reduced food effect", as used herein, refers to the food effect of a composition of an active substance which is less than 50%, preferably less than 40%, and more preferably less than 30%. The food effect is calculated by the formula defined above.

The term "positive food effect", as used herein, refers to a food effect where the AUC and/or $C_{max}$ is higher when the drug is administered orally in a fed state than when it is administered in a fasted state.

The term "negative food effect" refers to a food effect where the AUC and/or $C_{max}$ is lower when the drug is administered orally in the fed state than when it is administered in the fasted state. Drug-food interactions leading to a reduced incidence and/or severity of side effects are referred to as an "enhanced tolerability food effect".

The term "concomitantly with food" or "administration in the fed state", as used herein, refers to administration from about 30 minutes before a meal to about 1 hour after a meal.

The term "administration in the fasted state", as used herein, refers to administration at least 4 hours after a meal. Moreover, the fasted state also requires continued fasting for at least 2 hours after the administration.

The terms "sustained release" and "controlled release", as used herein, are used interchangeably in this application and refer to the release of a drug from a dosage form at such a rate that when a once-a-day dose or twice-a-day dose of the drug is administered in the sustained release or controlled release form, blood (e.g., plasma) concentrations (levels) of the drug are maintained within the therapeutic range but below toxic levels over a period of time from about 4 to about 24 hours.

The term "immediate release", as used herein, refers to the release of a drug from a dosage form within sixty minutes after administration to a subject.

The term "limited window of absorption", as used herein, refers to an oral bioavailability of less than about 75%, usually less than about 60%, usually decreasing with the increasing dose of a drug, and almost invariably having permeability/transit time limited absorption.

The term "release modifier", as used herein, refers to any excipient which modulates the release rate of a drug from a dosage form.

DETAILED DESCRIPTION OF THE INVENTION

In one embodiment, the present invention provides a controlled release pharmaceutical composition comprising an active agent, wherein said controlled release composition exhibits a reduced food effect as compared to conventional controlled release compositions of the active agent.

The active agent generally has a limited window of absorption and displays a negative food effect when an immediate release formulation of said active agent is orally administered to a subject.

The food effect of the compositions may be measured by AUC, $C_{max}$ and/or $T_{max}$ values.

In a preferred embodiment, the active agent is metformin or a pharmaceutically acceptable salt of metformin. Surprisingly, the novel controlled release compositions of metformin of the invention exhibit reduced food effect. Specifically, the food effect as measured by AUC is less than 50%, preferably less than 40%, and more preferably less than 30%.

In one embodiment, the controlled release pharmaceutical composition of the invention comprises a sustained release layer and an immediate release layer.

In a preferred embodiment, the invention provides a controlled release pharmaceutical composition comprising:

(a) a sustained release layer comprising:
  (i) an active agent, wherein said active agent has a limited window of absorption and displays a negative food effect when an immediate release formulation of said active agent is orally administered to a subject;
  (ii) optionally, at least one release modifier; and
  (iii) at least one sustained release agent; and
(b) an immediate release layer comprising said active agent and at least one pharmaceutically acceptable excipient, wherein said controlled release pharmaceutical composition exhibits reduced food effects.

In a preferred embodiment, the pharmaceutical compositions of the invention have the following amounts of the ingredients:

| Ingredient | Preferred (w/w) | More preferred (w/w) |
|---|---|---|
| | (weight % based on each layer) | |
| Sustained release layer: | | |
| active agent (ex., metformin) | 30-90% | 50-90% |
| release modifier | 0-20% | 1-10% |
| sustained release agent | 10-50% | 20-50% |
| Immediate release layer | | |
| active agent (ex., metformin) | 50-99% | |
| excipients | 1-50% | |

In one embodiment of the invention, the ratio of the active agent in the sustained release layer and the immediate release layer is between about 1:10 and about 10:1, preferably between about 2:8 and about 8:2, most preferably between about 3:7 and about 7:3.

In some embodiments, the compositions of the invention may be in the form of a bi-layer tablet. The immediate layer may either surround the sustained release layer or be located at the top or the bottom of the sustained release layer.

In some embodiments of the invention, the compositions may optionally contain at least one release modifier. Examples of release modifiers include but are not limited to alkaline agents and surfactants. Examples of the preferred alkaline agents include, but are not limited to, sodium phosphate, potassium phosphate, calcium phosphate, sodium hydroxide, sodium tartrate and sodium succinate. Examples of surfactants include, but are not limited to, sodium lauryl sulfate and Polysorbate 80. In a preferred embodiment, the release modifier is a phosphate salt.

In some embodiments of the invention, the compositions may optionally include at least one sustained release agent.

Examples of sustained release agents include, but are not limited to, hydrophilic polymers, hydrophobic polymers and wax materials.

Hydrophilic polymers which may be employed in the invention include, but are not limited to, hydroxypropylmethylcellulose, hydroxypropylcellulose, sodium carboxymethylcellulose, carboxymethylcellulose calcium, ammonium alginate, sodium alginate, potassium alginate, calcium alginate, propylene glycol alginate, alginic acid, polyvinyl alcohol, povidone, carbomer, potassium pectate, potassium pectinate, and the like.

Hydrophobic polymers which may be employed in the invention include, but are not limited to, ethyl cellulose, hydroxyethylcellulose, ammonio methyacrylate copolymer (Eudragit® RL or Eudragit® RS), methacrylic acid copolymers (Eudragit® L or Eudragit® S), methacrylic acid-acrylic acid ethyl ester copolymer (Eudragit® L 100-5), methacrylic acid esters neutral copolymer (Eudragit® NE 30D), dimethylaminoethylmethacrylate-methacrylic acid esters copolymer (Eudragit® E 100), vinyl methyl ether/maleic anhydride copolymers, their salts and esters (Gantrez®).

Wax materials which may be employed in the invention include, but are not limited to, beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glyceryl monooleate, acetylated monoglycerides, tristearin, tripalmitin, cetyl esters wax, glyceryl palmitostearate, glyceryl behenate, and hydrogenated castor oil.

In a preferred embodiment, the sustained release agent is a hydrophilic polymer such as hydroxypropylmethylcellulose.

Other excipients which may function as fillers, binders, lubricants, disintegrants, and plasticizers may also be included within either the sustained release layer and/or the immediate release layer.

In one embodiment, the composition of the invention may contain 0-20% w/w of a binder, 0-50% w/w of filler, 0-5% w/w of a lubricant, 0-5% w/w of a disintegrant or 0-20% w/w of a plasticizer in the sustained release layer and/or immediate release layer.

When the active agent is metformin, the total dose of metformin in the compositions of the invention can be equivalent to 250-2500 mg metformin hydrochloride, preferably from 250 mg to 1500 mg, and more preferably from 500 mg to 1000 mg.

When necessary, an additional active agent may be included to achieve the desired therapeutic effect. For example, when the active agent is metformin, another antihyperglycemic agent may be included with the immediate release layer with metformin.

It has been known that the first line blood glucose lowering therapy of type II diabetes is metformin or sulfonylurea monotherapy. If first line treatment is unsatisfactory, patients may be moved to second line combination therapies such as metformin with sulfonylurea or other antihyperglycemic agents. Accordingly, a second drug may be added to the formulations of invention to maximum the therapeutic efficacy. The second drug may be selected from currently available anti-hyperglycemic drugs and/or investigational anti-hyperglycemic drugs.

Examples of currently available antihyperglycemic drugs include, but are not limited to, sulfonylurea, biguanides, alpha-glucosidase inhibitors, thiazolidinediones (TZDs), dipeptidyl peptidase-4 inhibitors (DPP-4 inhibitors), meglitinides, glucagon-like peptide-1 analogs (GLP-1 analogs) and insulin. More specifically, the antidiabetic drugs include, but are not limited to, metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, repaglinide, nateglinide, mitiglindine, exenatide, liraglutide, albiglutide and insulin.

Examples of investigational anti-hyperglycemic drugs include, but not limited to, IL-1 modulators, Sodium-glucose transporter-2 (SGLT-2) inhibitors, Dual-PPAR modulators, 11β11-beta-hydroxysteroid dehydrogenase (HSD) inhibitors, CCR2 antagonists, selective inhibitors of fructose 1,6-bisphosphatase, immune modulators, cortisol synthesis inhibitors, Gastrin-Releasing Peptide (GRP) receptor agonists, G protein-coupled receptor 119 (GPR 119) agonists, Toll-like receptor-4 (TLR-4) agonists, FXR antagonists, and antisense drugs targeting glucagon receptors. More specifically, the investigational drugs include, but are not limited to, rhein, diacerein, monoacetylrhein, berberine, dapagliflozin, remogliflozin, etabonate, canagliflozin, and Aleglitazar.

The compositions of the invention may be administered twice-a-day or once-a-day.

In some embodiments, the invention provides a method of reducing the food effect of a controlled release composition comprising formulating an active agent of said controlled release composition into a unit dosage form, wherein said unit dosage form comprises at least one sustained layer and one immediate release layer. The method of reducing food effect is especially suitable for an active agent which has a limited window of absorption and displays a negative food effect when an immediate release dosage form of the active agent is orally administered to a subject. Preferably, the ratio of the active agent in the sustained release layer and immediate release layer is between about 1:10 and about 10:1, more preferably between about 3:7 and about 7:3.

It was surprisingly found that when the compositions of the present invention which included metformin were administered to patients with food, the bioavailability of metformin did not increase more than 50% as compared to the controlled release composition of metformin orally administered to patients in the fasted state. This result is an improvement as compared to commercially available extended release compositions including metformin such as Fortamet®, Glucophage® XR and Glumetza®.

It was also surprisingly found that when metformin was formulated into a dosage form comprising a sustained release layer and an immediate release layer, the bioavailability of metformin is improved in a fasted mode as compared to a comparable dose of a commercially available product such as Fortamet®, Glucophage® XR and Glumetza®.

Thus, in one embodiment, the present invention provides a method of improving bioavailability of a controlled release dosage form of metformin in a fasted state.

In a preferred embodiment, the invention provides a controlled release composition of metformin with improved bioavailability as compared to the administration of a comparable dose of a Fortamet® tablet in a fasted mode. Administering the inventive controlled release compositions of metformin allows one to reduce the time necessary to reach a steady state in a subject in need thereof.

Thus, in one embodiment, the present invention provides a method of reducing the time necessary to reach a steady state for metformin in a subject in need thereof comprising administering to said subject the compositions of the present invention. In one embodiment, the present invention provides a method of reducing the time necessary to reach a steady state for metformin in a subject in need thereof in the fasted state.

The controlled release compositions in accordance with this invention can be prepared by common methods well known to those skilled in the art of manufacturing drug compositions.

However, a traditional manufacturing process may be not applicable when a controlled release composition contains a higher dose of an active ingredient. For example, a traditional manufacturing process is not suitable for manufacturing a matrix controlled release tablet containing more than 750 mg of an active ingredient. A matrix controlled release table usually requires at least 10% by weight of total weight of a controlled release agent. A combination of high dose of active ingredients, controlled release agent(s) and other excipients results in a higher total weight of a tablet. When compressed by a traditional method, the tablet size may be too big and not suitable for swallow.

The present invention surprisingly resulted in reduced tablet size of a matrix controlled release tablet. In a preferred embodiment, the method of the invention comprises the following steps:

(a) mixing an acid salt form of active ingredient with an alkaline agent to form a mixture;

(b) granulating said mixture with a controlled release agent; and (c) compressing the granules from step (b) into tablets.

The method of reducing tablet size of the invention is especially suitable for a controlled release tablet comprising more than 750 mg of an active ingredient. By mixing an alkaline agent with an acid salt form of an active ingredient, the required amount of the controlled release agent may be decreased but still able to achieve the desired controlled release results. Accordingly, the size of the controlled release tablet is reduced. In a preferred embodiment, the method is suitable for a controlled release tablet comprising about 750-1250 mg of metformin HCl.

The following Examples are provided solely for illustrative purposes and are not meant to limit the invention in any way.

Example 1

A. Preparation of a Controlled Release Composition

A controlled release tablet containing 1000 mg of metformin HCl was prepared as follows:
(a) Sustained Release Layer

| Sustained release layer | | |
|---|---|---|
| Ingredients | mg/tablet | % |
| Metformin HCl | 600.0 | 59.4 |
| HPMC K100M CR (intra) | 50.0 | 5.0 |
| HPMC K100LV CR | 4.5 | 0.4 |
| $Na_2HPO_4$ | 50.0 | 5.0 |
| HPMC K100M CR (extra) | 300.0 | 29.7 |
| Magnesium stearate | 5.0 | 0.5 |
| Subtotal | 1009.5 | 100.0 |

HPMC K100LV CR was dissolved in purified water as a binder solution. Metformin HCl, $Na_2HPO_4$ and partial HPMC K100M CR (intra) were blended and passed through a 30 mesh screen. The blended powders were wet granulated in a high shear mixer by sparing with the binder solution. The granules were dried in a fluidized bed granulator at 70° C. until the loss on drying is not more than 3%. The dried granules were passed through a Comil equipped with a 20# mesh screen. The HPMC K100M CR (extra) was passed through 30# mesh screen and blended with the dried granules by a V-blender. Magnesium stearate was passed through 30# mesh screen and blended with the mixtures.

(b) Immediate Release Layer

| Immediate release layer | | |
|---|---|---|
| Ingredients | mg/tablet | % |
| Metformin HCl | 400.0 | 73.4 |
| Microcrystal cellulose | 100.0 | 18.3 |
| Hydropropyl cellulose (Klucel ® EF) | 15.0 | 2.8 |
| Ac-Di-Sol | 25.0 | 4.6 |
| Magnesium stearate | 5.0 | 0.9 |
| Subtotal | 545.0 | 100.0 |

Klucel® EF was dissolved in purified water as a binder solution. Metformin HCl and Microcrystal cellulose were blended and passed through a 30# mesh screen. The blended powders were wet granulated in a high shear mixer by sparing with the binder solution. The granules were dried in a fluidized bed granulator at 70° C. until the loss on drying is not more than 3%. The dried granules were passed through a Comil equipped with a 20# mesh screen. Ac-Di-Sol was passed through 30# mesh screen and blended with the dried granules by a V-blender. Magnesium stearate was passed through 30# mesh screen and blended with the mixtures.

(c) Compression

The sustained release and immediate release mixtures were compressed to form a capsule shaped tablet.

The size of the capsule shaped table of the invention is 21.5 mm×12.0 mm. The thickness is 8.25 mm. The shape of Fortamet® 1000 mg is round. Its diameter is 8.73 mm and thickness is 12.98 mm. The table size and shape of the invention is more suitable for swallow when compared to Fortamet®.

B. Dissolution Test

The tablets were tested in an USP type II apparatus at 50 rpm in 900 ml of simulated gastric fluid (0.1 HCl). The result was as follows:

| 0.1N HCl, 900 mg, USP Apparatus II with sinker, 50 rpm | |
|---|---|
| Time (hr) | % metformin released |
| 0 | 0.0 |
| 0.5 | 46.3 |
| 1 | 57.5 |
| 2 | 68.7 |
| 4 | 82.7 |
| 6 | 91.6 |
| 8 | 97.1 |
| 10 | 100.0 |

C. Bioavailability Study

Study Design

A crossover bioavailability study to compare metformin HCl 1000 mg controlled release tablets of the invention and Fortamet® in healthy subjects.

Blood Samples Schedule

Pre-dose (0 h) and 1, 2, 3, 4, 5, 6, 8, 10, 12 and 14 hours post dose for test drugs and reference drugs with heparinized tubes.

| Bioavailability study of the metformn CR formulation (1000 mg) of the invention and Fortamet ® (1000 mg) | | | | |
|---|---|---|---|---|
| | Fed (n = 7) | | Fasted (n = 7) | |
| PK parameters | Test | Fortamet ® | Test | Fortamet ® |
| $C_{max}$ (ng/ml) | 1491.9 (13%) | 1819.6 (13%) | 1812.1 (18%) | 1116.0 (43%) |
| $AUC_{0-14}$ (ng · h/ml) | 15270 (10%) | 15015 (12%) | 11337 (16%) | 6470 (36%) |
| $AUC_{0-\infty}$ (ng · h/ml) | 15579 (10%) | 15358 (11%) | 11896 (15%) | 7020 (36%) |
| $T_{max}$ (hr) | 4.6 (4-6) | 5.4 (5-6) | 3.7 (2-4) | 3.9 (2-5) |
| $T_{1/2}$ (hr) | 3.8 (3.3-4.4) | 4.0 (3.2-4.4) | 2.7 (2.3-3.1) | 3.2 (2.8-3.8) |

The invention claimed is:

1. A controlled release pharmaceutical composition with a reduced food effect, said composition comprising a sustained release layer and an immediate release layer, wherein metformin or a pharmaceutically acceptable salt thereof is incorporated into said sustained release layer and said immediate release layer at a weight ratio from about 1:10 to about 10:1 and wherein said controlled release pharmaceutical composition further comprises at least one pharmaceutically acceptable excipient.

2. The controlled release pharmaceutical composition of claim 1, wherein the food effect is less than 50%.

3. The controlled release pharmaceutical composition of claim 2, wherein the food effect is less than 40%.

4. The controlled release pharmaceutical composition of claim 3, wherein the food effect is less than 30%.

5. The controlled release pharmaceutical composition of claim 1, wherein the sustained release layer comprises at least one sustained release agent and, optionally, at least one release modifier.

6. The controlled release pharmaceutical composition of claim 1, wherein said composition further comprise a second active agent.

7. The controlled release pharmaceutical composition of claim 6, wherein said second active agent is selected from currently available antihyperglycemic drugs and investigational antihyperglycemic drugs.

8. The controlled release pharmaceutical composition of claim 7, wherein said currently available antihyperglycemic drugs include, but are not limited to, sulfonylurea, biguanides, alpha-glucosidase inhibitors, thiazolidinediones (TZDs), dipeptidyl peptidase-4 inhibitors (DPP-4 inhibitors), meglitinides, glucagon-like peptide-1 analogs (GLP-1 analogs) and insulin.

9. The controlled release pharmaceutical composition of claim 7 wherein the antihyperglycemic drugs include, but are not limited to, metformin, glyburide, glimepiride, glipyride, glipizide, chlorpropamide, gliclazide, acarbose, miglitol, pioglitazone, troglitazone, rosiglitazone, isaglitazone, muraglitizar, peliglitazar, sitagliptin, saxagliptin, vildagliptin, alogliptin, linagliptin, dutogliptin, repaglinide, nateglinide, mitiglindine, exenatide, liraglutide, albiglutide and insulin.

10. The controlled release pharmaceutical composition of claim 7, wherein said investigational antihyperglycemic drugs include, but not limited to, IL-1 modulators, Sodium-glucose transporter-2 (SGLT-2) inhibitors, Dual-PPAR modulators, 11β11-beta-hydroxysteroid dehydrogenase (HSD) inhibitors, CCR2 antagonists, selective inhibitors of fructose 1,6-bisphosphatase, immune modulators, cortisol synthesis inhibitors, Gastrin-Releasing Peptide (GRP) receptor agonists, G protein-coupled receptor 119 (GPR 119) agonists, Toll-like receptor-4 (TLR-4) agonists, FXR antagonists, and antisense drugs targeting glucagon receptors.

11. The controlled release pharmaceutical composition of claim 10, wherein the investigational drugs include, but are not limited to, rhein, diacerein, monoacetylrhein, berberine, dapagliflozin, remogliflozin, etabonate, canagliflozin, and Aleglitazar.

12. A controlled release pharmaceutical composition comprising:
(a) a sustained release layer comprising:
(i) metformin or a pharmaceutically acceptable salt thereof;
(ii) optionally, at least one release modifier; and
(iii) at least one sustained release agent; and
(b) an immediate release layer comprising said metformin and at least one pharmaceutically acceptable excipient;
wherein said composition exhibits reduced food effect.

13. The controlled release pharmaceutical composition of claim 12, wherein said composition further comprises a second active agent in the immediate layer.

14. The controlled release pharmaceutical composition of claim 12, wherein said composition further comprises a second active agent in the sustained release layer.

15. The controlled release pharmaceutical composition of claim 12, wherein the release modifier is an alkaline agent or a surfactant.

16. The controlled release pharmaceutical composition of claim 12, wherein the release modifier is a phosphate salt.

17. The controlled release pharmaceutical composition of claim 12, wherein the sustained release agent is selected from the group consisting of a hydrophilic polymer, a hydrophobic polymer, a wax and the combination thereof.

18. The controlled release pharmaceutical composition of claim 12, wherein the sustained release layer contains about 30-90% w/w of said metformin, 0-20% w/w of said release modifier, and 10-50% w/w of said sustained release agent.

19. The controlled release pharmaceutical composition of claim 12, wherein the sustained release layer contains 50-90% w/w of said metformin, 1-20% w/w of said release modifier and 20-50% w/w of said sustained release agent.

20. The controlled release pharmaceutical composition of claim 12,
wherein the food effect is less than 50%.

21. The controlled release pharmaceutical composition of claim 12, wherein the food effect is less than 40%.

22. The controlled release pharmaceutical composition of claim 12, wherein the food effect is less than 30%.

23. The controlled release pharmaceutical composition of claim 12, wherein the food effect is less than 50% in AUC.

24. The controlled release pharmaceutical composition of claim 12 wherein the food effect is less than 40% in AUC.

25. The controlled release pharmaceutical composition of claim 12, wherein the food effect is less than 30% in AUC.

26. A controlled release pharmaceutical composition of metformin, wherein said controlled release pharmaceutical composition comprises a sustained release layer and an immediate release layer, wherein metformin or a pharmaceutically acceptable salt thereof is incorporated into said sustained release layer and said immediate release layer, at a weight ratio from about 1:10 to about 10:1 and wherein the bioavailability of metformin is not increased more than 50% when said controlled release pharmaceutical composition is orally administered to a subject in the fed state.

27. A controlled release pharmaceutical composition comprising:
(a) a sustained release layer comprising:
(i) 50-90% w/w of metformin or a pharmaceutically acceptable salt thereof;
(ii) 20-50% w/w of a hydrophilic polymer; and
(iii) a phosphate salt; and
(b) an immediate release layer comprising:
(i) 50-90% w/w of metformin or a pharmaceutically acceptable salt thereof; and
(ii) 1-50% w/w of a pharmaceutically acceptable excipient;
wherein said composition exhibits reduced food effect.

* * * * *